United States Patent [19]

Hoye et al.

[11] Patent Number: 5,284,555
[45] Date of Patent: Feb. 8, 1994

[54] PROCESS FOR PREPARING ORGANOPHOSPHINES

[75] Inventors: Peter A. T. Hoye, Stourbridge; James W. Ellis, Woodloes Park, both of England

[73] Assignee: Albright & Wilson Limited, Warley, England

[21] Appl. No.: 919,730

[22] Filed: Jul. 24, 1992

[30] Foreign Application Priority Data

Aug. 15, 1991 [GB] United Kingdom ............. 9117603

[51] Int. Cl.$^5$ ............................................. C07F 9/00
[52] U.S. Cl. ............................. 204/157.6; 204/157.73
[58] Field of Search ......... 204/157.15, 157.6, 157.64, 204/157.73

[56] References Cited

U.S. PATENT DOCUMENTS

| | | | |
|---|---|---|---|
| 2,803,597 | 8/1957 | Stiles et al. | 204/157.73 |
| 3,435,076 | 3/1969 | Mason et al. | 204/157.73 |
| 4,613,699 | 9/1986 | Green | 568/15 |

FOREIGN PATENT DOCUMENTS

WO84/04923 12/1984 PCT Int'l Appl. .

OTHER PUBLICATIONS

Rauhut et al, *J. Org. Chem.*, vol. 26, pp. 5138 and 5140; vol. 24, p. 5144.

*Primary Examiner*—John Niebling
*Assistant Examiner*—Cybille Delacroix-Muirheid
*Attorney, Agent, or Firm*—Frishauf, Holtz, Goodman & Woodward

[57] ABSTRACT

Olefins can be induced to react with phosphines at ambient temperature and pressure to produce organophosphines by free-radical addition. Suitable olefins include $C_1$ to $C_4$ alpha-olefins, cyclic olefins, polycycloalkenyl species, allyl alcohol and esters of vinyl phosphonic acid.

16 Claims, No Drawings

PROCESS FOR PREPARING ORGANOPHOSPHINES

This invention relates to the preparation of organophosphorus compounds and in particular to organophosphines.

The possible uses of organophosphine products based on alkyl substituted derivatives of phosphine described in the literature are wide ranging and numerous. For example, trioctylphosphine is oxidised with hydrogen peroxide solution to form the compound $(C_8H_{17})_3PO_4$ commonly known as trioctylphosphine oxide (or as the acronym TOPO). The product is used in two different extraction processes—firstly in the extraction of uranium (VI) from crude phosphoric acid, and secondly in the extraction of dilute acetic acid from the effluent that results from cellulose manufacture or the production of acetaldehyde.

Tributylphosphine is reacted with alkyl or aryl halides to form the corresponding phosphonium halides e.g. $(C_4H_9)_3P^+\text{-R Hal}^-$. These are highly polar, stable species which find application as phase transfer catalysts, biocides (especially as a constituent of anti-fouling paints), salt-like solvents, plant growth regulators and promoters in carbonylation reactions, and catalysts in the reactions Of $P_4S_{10}$ with alcohols.

Other significant examples include the reaction product of $PH_3$ and cyclooctadiene and of $PH_3$ and di-isobut-1-ene respectively. The former may be (i) converted with eicosene into a corresponding tertiary phosphines, which is used as a ligand in the cobalt-catalysed hydroformylation of $C_{12}/C_{14}$—linear olefins, and (ii) converted into a nickel complex of a phosphinoacetic acid thereby furnishing an important catalyst in the process of ethene oligomerisation. Bis-(2, 4, 4-trimethylpentyl-) phosphinic acid, available by oxidation of the secondary phosphine generated by the reaction of $PH_3$ and 2, 4, 4-trimethylpentyl-1 is used for extractive Co/Ni separation.

The synthesis of such organophosphines is described in the prior art, the preferred process (in view of industrial applicability) being the free-radical initiated addition of phosphine to olefins. Compared with such alternatives as the "Grignard route" from $PCl_3$ and alkyl magnesium halide, which leads to considerable by-product formation in unpredictable amounts, the free-radical initiated route offers greater selectivity, via process control to obtain the desired organophosphine.

However, it has hitherto been considered necessary, in the context of this process, to employ elevated temperatures, and high pressures for the reaction of olefins with phosphine. Temperatures of 80° C. and above, (e.g. 100° C.) are described in PCT/US84/0084 and U.S. Pat. No. 4,613,399, and Rauhut et al (J. Org. Chem, vol 26, 5138) describes the implementation of elevated pressures to increase the solubility of phosphine in the liquid phase. Typically, the industrial production of alkyl phosphines from the radical initiated addition of phosphine to olefin is carried out in a high- pressure reactor. Consequently, numerous safety hazards have to be overcome in view of the high toxicity and spontaneous flammability of $PH_3$ when under pressure.

This means that there are numerous useful organophosphorus products derivable from this route whose use on a commercial scale is still narrowly restricted owing to the handling and processing problems associated with $PH_3$.

Clearly it would be desirable to operate at lower pressures and temperatures than those deemed necessary hitherto. According to the prior art, radical initiated addition of phosphine to olefin at ambient temperature and pressure has only been contemplated where the olefin is an alkenyl carboxylate, such as vinyl acetate, which constitutes a highly reactive monomer. This is disclosed in GB 1 492 514. Subsequent teachings indicate that this idea has been discarded in favour of the implementation of more forcing conditions as above described, especially where "inert" olefins (such as unfunctionalised linear alpha-olefins and cyclic olefins) are used. These "inert" olefins are the desired precursors of the relatively few industrially and commercially important species listed hereinabove.

We have now discovered that, contrary to the teachings of the more recent prior art, olefins can be induced to react with phosphines at ambient temperature and normal atmospheric pressure to produce, by means of free-radical addition, organophosphine in high yield. This is unexpected, and, furthermore, provides a safe, economically-viable route to compounds whose considerable potential utility is at present unexploited owing to the hazards involved in high-pressure and/or high-temperature syntheses.

Thus, the present invention provides a process for the preparation of organophosphines, said process comprising reacting (i) a phosphine with (ii) an ethylenically-unsaturated alicyclic hydrocarbon, aliphatic hydrocarbon, alcohol or vinyl phosphonic acid ester in the presence of a free radical initiator.

The present invention also provides an organophosphine made by the process described in the immediately-preceding paragraph.

Typically, the phosphine has the general formula $R^1R^2PH$ wherein $R^1$ and $R^2$, which may be the same or different, are: hydrogen, alkyl, aryl, cycloalkyl or aralkyl. Preferably $R^1$ and $R^2$ are hydrogen. Exemplary ethylenically-unsaturated alicyclic or aliphatic hydrocarbons or alcohols include linear alpha-olefins having four or more carbon atoms, such as but-1-ene, hex-1-ene and oct-1-ene, branched olefins such as di-isobut-1-ene, cyclic olefins having six or more carbon atoms such as cyclohexene, cyclooctadiene, polycycloalkenyl species such as dicyclopentadiene, norbornene and norbornadiene and hydroxy or cyano derivatives of any of the above, such as allyl alcohol and esters of vinyl phosphonic acid.

Free-radical initiating catalysts, known per se and suitable for use in the process of the present invention, include peroxidic radical-forming agents and azo compounds, such as di-tert-butyl peroxide and azo-bis-isobutyronitrile respectively. Azo-bis-dimethylvaleronitrile is particularly preferred.

The reaction may be initiated by the decomposition of the radical-initiator, for example thermally or by means of a source of radiation, such as ultraviolet light of wavelength 300–400 nM, e.g. 365 nM. Preferably an ultraviolet lamp is suitably positioned relative to the reactor.

When using UV radiation the temperature within the reaction vessel ranges typically from −50° C. to 60° C., this being to a certain extent dependant on the nature and reactivity of the ethylenically unsaturated hydrocarbon present. Preferably, the reaction is carried out, by UV irradiation at ambient temperature. Alternatively, the reaction vessel may be heated (e.g. to 80° C.), in order to activate the free radical source (by thermochemical decomposition) and catalyse the reaction.

If desired the reaction may be carried out in a relatively inert, normally liquid organic solvent of which aromatic hydrocarbons such as toluene or xylene are suitable examples. Typically, phosphine is bubbled through a solution containing the ethylenically-unsaturated hydrocarbon or alcohol. The organophosphine products obtained thereby can then be isolated by evaporating off any solvent, leaving the organophosphine product as a residue, followed by work up.

Usually, this yields a mixture of mono, di and tri-organo substituted phosphines, the product distribution being to a certain extent dependent on the constitution and configuration of the ethylenically-unsaturated hydrocarbon or alcohol, although it is not intended that the present, invention be construed with reference to any particular theory.

Wherein it is desired to bias said product distribution towards those organophosphines with a greater degree of organo-substitution, e.g. to furnish a product mixture comprising predominantly tertiary organophosphines, the reaction may be carried out in two stages, typically with product derived as hereinabove described, thus constituting a first stage, being further reacted with the appropriate ethylenically unsaturated hydrocarbon or alcohol in the presence of a free radical source in the absence of phosphine and under the conditions as hereinabove described, to yield organophosphine product which may be isolated as hereinbefore described.

Preferred embodiments of the present invention will be illustrated by way of the following Examples:

EXAMPLES 1-11

Example 1

Synthesis of trioctylphosphine and TOPO

Octene-1 (500 mls=360 g) was placed in a stirred one liter reactor and the system purged with nitrogen. Phosphine at atmosphere pressure was passed into the well stirred solution at 18° C. at an initial rate of 450 mls/min until the solution was saturated. A solution of 2,2'-diazo bis (2,4-di-methyl valeronitrile), (azo initiator), (1 g in 10 mls octene) was added, and the solution irradiated with light from a black-light ultra-violet lamp having maximum radiation at 365 mm to cleave the azo initiator whilst passing phosphine to balance to rate of its reaction. The solution was cooled to maintain the temperature at 25°-30° C.

Analysis of a small portion of the reactants by $^{31}$Pnmr after 2.5 hours showed the bulk of the olefin had been converted to trioctylphosphine. Azo initiator (1 g in 10 mls octene-1) was added and reaction continued for a further 3 hours at 28° C., after which time nitrogen was passed to remove the bulk of unreacted dissolved phosphine. Analysis at this stage indicated trioctylphosphine—97%, dioctyl phosphine—2.3%, and mono octyl phosphine 0.7% on a phosphorus w/w basis.

Octene-1 (80 mls=58 g) was added and irradiation continued for one hour at ambient temperature after which time analysis indicated trioctylphosphine with below 1% dioctylphosphine.

Water (30 mls) and methylated spirits (150 mls) were added to the well stirred solution and the phosphine oxidised by slow addition of 30% hydrogen peroxide whilst keeping the temperature below 30° C. by cooling.

Work up yielded trioctylphosphine oxide, a colourless solid FP 47.0° C., 365 g—75% yield on the octene used.

Example 2

Synthesis of Trioctylphosphine

Octene-1 (700 mls=505 g) was placed in a stirred one liter stirred reactor, cooled to −20° C. and flushed with nitrogen. The solution was saturated with phosphine at atmospheric pressure by passing in PH$_3$ gas at 200 mls/min for 20 minutes. A solution of 2,2'-diazo bis (2,4-dimethylvaleronitrile) (1 g in 10 mls octene-1) was added. The solution was irradiated with UV light as in Example 1 while passing PH$_3$ to balance the rate of absorption, and keeping the temperature below −10° C. by cooling.

Analysis after two hours indicated the presence of trioctylphosphine 61.5 g, dioctylphosphine 61 g, and monoctylphosphine 30.4 g. A further 1g quantity of initiator was added after 2.5 hours. Analysis after 3.5 hours indicated the presence of trioctylphosphine 147 g., dioctylphosphine 65 g., and monooctylphosphine 28.5 g.

The reaction temperature was allowed to rise slowly over the next 2 hours to 18° C. The phosphine stream and UV light were switched off and a slow stream of nitrogen passed overnight to remove dissolved phosphine. Analysis indicated trioctylphosphine 362 g, dioctylphosphine 44.5 g., and monooctylphosphine 8.5 g. Octene-1 (100 mls) and azo initiator (1 g) were added and the solution irradiated for 2 hours at 16° C. Work up gave 430 g trioctylphosphine which by nmr analysis contained 1.1% (m/m) dioctylphosphine.

Example 3

Synthesis of trishydroxypropylphosphine oxide

Allyl/alcohol (425 g) was placed in a stirred one-liter reactor at ambient temperature and the apparatus and alcohol flushed with nitrogen. The alcohol was saturated with phosphine by passing PH$_3$ gas at atmospheric pressure for one hour.

A solution of 1 g 2,2'-diazobis (2,4-dimethylvaleronitrile) in 10 mls allyl alcohol was added and the solution irradiated with UV light as in Example 1 at 20°-25° C., whilst passing PH$_3$ to balance the rate of absorption. Further initiator (1 g) was added after 2.5 hours. After 4.5 hours the PH stream was stopped and replaced by a slow stream of nitrogen. Illumination was continued for a further 4 hours.

$^{31}$Pnmr showed the product to consist of tris hydroxypropyl phosphine having a chemical shift of—29.7 ppm (65.5% m/m), bis hydroxypropyl phosphine—67.3 ppm (3% m/m) and telomeric tertiary phosphines (31.5% m/m).

Oxidation with hydrogen peroxide yielded 270 g of phosphine oxides which crystallised to a hard solid. Recrystallisation of 157 g of this product mixture from isopropanol (400mls) gave 96 g of tris hydroxypropyl phosphine oxide, a colourless solid mp 109° C., $^{31}$Pnmr, +60.5 ppm. Found:P-13.3%; Calc. P-13.9%.

Example 4

Synthesis of tributylphosphine and tetrabutylphosphonium bromide

Butene-1 (600 mls) was condensed into a cooled nitrogen filled one liter reactor fitted with an alcohol/solid CO$_2$ condenser and magnetic stirrer. The mixture was saturated with phosphine at −15° C. by passing $PH_3$ gas at 100 mls/min. for 30 minutes.

A solution of 2,2'-diazobis(2,4-dimethylvaleronitrile) (2 g in 8 mls toluene) was added and the solution irradiated with UV light for 6.5 hours. During this time the reaction temperature was maintained at −10° C. for 3 hours and then allowed to rise slowly to −5°C. Phosphine was passed so as to maintain a slight positive flow through the solution for 6 hours and then replaced by a nitrogen stream.

Further azo initiator additions (1 g in 4 mls toluene) were made at 1.5 hour intervals.

The solution was allowed to warm to ambient temperature (12° C.) overnight during which time unreacted $PH_3$ and part of the butene-1 were removed. Analysis of a portion of solution indicated the presence of $Bu_3P$-65 g., $Bu_2PH$ 16.5 g and $BuPH_2$ 5.2 g.

Azo initiator (0.5 g) was added and the solution irradiated at 10°-15° C. for 5 hours to give tributylphosphine which contained 1.3% (m/m) $Bu_2PH$, 0.86% (m/m) di-n-butyl 2-butylphosphine and 0.27% (m/m) di n-butyl sec-butylphosphine.

Toluene (200 mls) and butyl bromide (150 g) were added and the solution heated to reflux. Work up yielded tetrabutyl phosphonium bromide 147 g.

Example 5

Preparation of trihexylphosphine

Hexene-1 (252 g. 3 moles) was purged with nitrogen for two hours before saturating with phosphine. 2,2'-Diazobis(2,4 dimethylvaleronitrile), (1.0 g, 4 mmol) in toluene (2 ml) was added and phosphine passed through the solution for six hours. The solution temperature was maintained at 20° C. and irradiated with ultra-violet light from a 365 nm black light mercury vapour lamp throughout to cleave the azo initiator. Further 1 g aliquots of initiator in toluene were added every ninety minutes.

At the end of the reaction the phosphine was flushed from the system with nitrogen. The addition of further azo initiator and subsequent irradiation with UV light for three hours aged the product, reacting any hexylphosphine and dihexylphosphine through to the required trihexylphosphine product.

The trihexylphosphine was vacuum distilled, first removing the volatile components before collecting the fraction which boiled at 140° C.@0.9 mmHg. The yield was 244 g, an 88% conversion of the starting olefin. The product was a clear mobile oil with $^{31}$Pnmr=−30.7 ppm and $^{13}$Cnmr according to the expected structure.

Example 6

Preparation of mixed hexyl/octyl/desyl phosphine oxide

Hexene-1(84 g, 1 mole), octene-1 (112 g. 1 mole) and decene-1 (140 g, 1 mole) were deoxygenated by passing nitrogen for two hours. 2,2'-Diazobis-(2,4-dimethylvaleronitrile (1.0 g, 4 mmol) in toluene (3 ml) was added and whilst maintaining the reaction temperature at 20° C. and irradiating with 365 nm UV light phosphine was passed through the solution for six hours. Further aliquots of azo initiator (1.0 g, 4 mmol) in toluene (3 ml) were added every ninety minutes.

The phosphine was purged from the solution with nitrogen before aging the product (as in example 5 above) for three hours. After removing the volatiles in vacuo the yield of mixed hexyl/octyl/decyl phosphine was 332 g, a 90% conversion of the starting olefin.

Oxidation with hydrogen peroxide followed by workup gave hexyl/octyl/decyl phosphine oxide as a clear mobile oil. $^{31}$Pnmr=49.4 ppm Found: %P=7.82%: calc. %P=8.03%.

Example 7

Preparation of dinorbornyl phosphine

Norbornene (194 g. 2.06 moles) and toluene (100 ml) were deoxygenated by passing nitrogen through the solution for two hours. Phosphine was then passed into the solution for three hours, adding 2,2'-diazobis-(2,4-dimethylvaleronitrile) (0.5 g, 2 mmol) at the start of the reaction and every fifty minutes subsequently. The reaction mixture was irradiated with 365 nm U.V. light throughout, and absorbed phosphine at up to 300 ml.min$^{-1}$ before tailing off towards the end of the reaction.

After purging with nitrogen to remove any unreacted phosphine the product solution was cooled to −20° C. and further norbornene (20 g. 212 mmol) and azo initiator (0.5 g. 2 mmol) added before irradiating for a further two hours to age the product, reacting primary phosphine through to the required secondary phosphine product. The $^{31}$Pnmr spectrum of the product at this stage showed it to contain 90% (m/m) of dinorbornylphosphine diastereomers with 10% (m/m) of trinorbornylphosphine diastereomers. These assignments were confirmed by G.C.M.S. studies.

The product was vacuum distilled first removing the volatile components before collecting the dinorbornylphosphine fraction at 118°-122° C.@0.2 mmHg. The yield of dinorbornylphosphine, a clear viscous oil which crystalised on cooling to 0° C. was 176 g, 77% based on the starting olefin, with $^{31}$Pnmr, $^{13}$Cnmr and G.C.M.S. according to the expected structure.

Example 8

Synthesis of liquid trioctylphosphine oxide

Hexene-1 (105 g, 1.25 moles), octene-1 (140 g, 1.25 moles) and decene-1 (175 g, 1.25 moles) were charged to a one liter four necked flask and deoxygenated by passing nitrogen for two hours. The resulting solution was heated to 65° C. and phosphine passed for six hours. 2,2'-diazobis (2,4-dimethylvaleronitrile) (1.0 g, 4 mmol) in toluene (3 ml) was added at the start of the phosphine addition with subsequent additions of 0.5 g in toluene (2 ml) every hour. Phosphine was absorbed at approx. 75 ml/min for four hours before tailing off. The product solution was allowed to cool and was purged with nitrogen for fifteen hours to remove unreacted phosphine form the system. The product was then reheated to 65° C. for a further three hours in the presence of a further 0.5 g of azo initiator to age the product, reacting residual primary and secondary phosphines through to the required tertiary phosphine product.

The mixed hexyl/octyl/decyl phosphine product was added to a mixture of distilled water (1 liter) and toluene (250 ml) and oxidised by the careful addition of hydrogen peroxide (130 g, 1.15 moles).

After workup the product was obtained as a colourless oil with $^{13}$Pnmr and $^{13}$Cnmr according to the expected structure. The yield was 363.5 g, 0.94 moles, which is a 75.3 % conversion of the starting olefins. Found: %P=7.39%. Calc: %P=8.03%.

Example 9

Preparation of trioctylphosphine oxide (TOPO)

Octene-1 (560 g, 5 moles) was charged to one liter vessel and deoxygenated by passing nitrogen for two hours. The solution was heated to 70° C. and saturated with phosphine before adding 2,2'-diazobis (2,4-dimethylvaleronitrile) (1.0 g, 4 mmol) in toluene (4 ml) and passing phosphine into the solution for 6.5 hours. Further aliquots of azo initiator (0.5 g, 2 mmol) in toluene (2 ml) were added every 50 minutes. The solution absorbed phosphine at approximately 100 mlmin$^{-1}$ for the first four hours before slowly tailing off.

At the end of the reaction the product was purged with nitrogen to remove unreacted phosphine before aging the product for three hours as described in example 8 above. The crude trioctylphosphine so obtained was oxidised with hydrogen peroxide (1.5 moles) before workup. The yield of trioctylphosphine oxide was 523 g, 1.35 mol, 81.3% based on the starting olefin. Mpt=47.5°–48.5° C. Found: %P=7.80%. Calc: %P=8.03%.

Example 10

Reaction of phosphine with norbornene

Norbornene (188 g, 2 moles) and toluene (60 g) were deoxygenated by passing nitrogen for two hours before heating to 70° C. and saturating with phosphine. 2,2'-diazobis(2,4-dimethylvaleronitrile) (0.5 g, 2 mmol) in toluene (2 ml) was added and phosphine passed into the solution for 3.5 hours, adding further of azo initiator every fifty minutes.

At the end of the reaction the product solution was cooled and purged with nitrogen to remove the residual phosphine before vacuum distilling the product. Dinorbornylphosphine was obtained as a clear viscous oil boiling at 118°–122° C.@0.2 mmHg. The yield was 146 g, 66% based on the starting olefin.

Trinorbornyl phosphine was obtained as a second fraction which distilled at 154° C.@0.2 mmHg and crystalised to give a white solid on cooling. The yield was 55.4 g, 25.9%.

Dinorbornylphosphine was characterised as the dithiophosphinic acid. $^{31}$Pnmr=85.8 ppm and 86.0 ppm (diastereomers). Mpt=99°–100° C. Found: %P=10.64%;calc=10.80%.

Trinorbornylphosphine was characterised as the phosphine sulphide: Mpt=299°–301° C. Found: %P=8.86%;calc=8.90%

Example 11

Reaction of phosphine with dicyclopentadiene

Dicyclopentadiene (inhibited with 200 ppm of p-tert-butylcatechol) (264 g, 2 moles) and toluene (60 ml) were deoxygenated by passing nitrogen for two hours. The resulting solution was heated to 70° C. and 2,2'-diazobis(2,4-dimethylvaleronitrile) (0.5 g, 2 mmol) added, before passing phosphine into the solution. Further additions of azo initiator (0.5 g, 2 mmol) were made every fifty minutes. After a thirty minute induction period the solution absorbed phosphine at 100–200 mlmin$^{-1}$ for ninety minutes before tailing off towards the end of the reaction.

Residual phosphine was purged from the product with nitrogen before stripping out the volatile components in vacuo. The dicyclopentadienyl phosphine product was obtained as a viscous oil, yield 266.4 g, a 93% conversion of the starting olefin.

The $^{31}$Pnmr of the product was complex showing ten resonances at $-38$ to $-27$ppm. None of these resonances exhibited a $^1J_{P-H}$ splitting in the proton coupled $^{31}$Pnmr spectrum, which implies that all the products are tertiary phosphines. The $^{13}$Cnmr and $^1$Hnmr showed that the products contained some unreacted double bonds. Phosphorus analysis on the product phosphine oxide gave % phosphorus=9.44%, an average of 2.1 dicyclopentadiene adducts per phosphorus.

Example 12

Reaction of phosphine with cyclooctadiene

Cyclooctadiene (234 g, 3 moles) was deoxygenated by passing nitrogen for three hours, before heating to 70° C. and passing phosphine into the solution 15.5 hrs. 2,2'-diazobis(2,4-dimethylvaleronitrile) was added in aliquots of 0.5–1.0 g every hour. Phosphine was absorbed very slowly (at approximately 20 mlmin$^{-1}$) throughout and at the end of the reaction ca. 65% of the cyclooctadiene had reacted. Examination of the product by the $^{31}$Pnmr showed that it contained the mixture of secondary and tertiary phosphines given in table 1 (below).

TABLE 1

| | Analysis of phosphine/cyclooctadiene Reaction Products by $^{31}$Pnmr | |
|---|---|---|
| Chemical Shift (ppm) | Amount Present (% m/m) | Assignment |
| −54.0 | 22.3 | 9-phosphabicyclo[3.3.1]nonane |
| −48.3 | 2.4 | 9-phosphabicyclo[4.2.1]nonane |
| −42.1−−33.3 | 10.4 | Other secondary phosphines |
| −23.3, −20.1, 15.7 and 16.3 | 64.3 in total | Tertiary phosphine products |

Example 13

Synthesis of tris-phosphonoethyl phosphine

A solution of vinyl di-isopropyl phosphonate (128 g) in toluene (200 ml) was placed in a stirred 500 ml flask and cooled to 5° C. whilst flushing with phosphine by passing PH$_3$ gas at atmospheric pressure, at 5° C. for 45 minutes.

A solution of 1 g 2,2'-diazo-bis(2,4-dimethyl valero nitrile) in toluene (10 ml) was added and the solution irradiated with an ultraviolet lamp (as in Example 1) whilst passing a steady stream of phosphine gas.

The reaction was exothermic and the temperature was maintained below 16° C. by cooling. Phosphine uptake ceased after 3.5 hours and the solution was then flushed with nitrogen to remove dissolved phosphine.

$^{31}$P nmr showed the product at this stage to consist of:

3.7% of the mono-adduct

2.1% of the bis-adduct

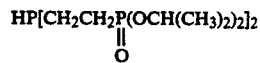

and the remainder of the tris-adduct

A further 6 g of vinyl di-isopropyl phosphonate was added and the solution again irradiated with ultraviolet light to complete the reaction of the mono- and di-phosphines The tris-adduct was characterised by $^{31}$P nmr:

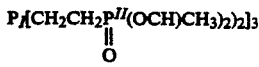

$P_I\delta = -19.1$ ppm; 1:3:3:1 quartet
$^3J_{P-P} = 49.6$ Hz
$P_{II}\delta = 29.4$ ppm; 1:1 doublet
$^3J_{P-P} = 49.6$ HZ
Relative integral of $P_I$:$P_{II}$ was 1:3

Concentrated hydrochloric acid (100 ml) was added and the solution stirred at reflux for 10 hours whilst distilling off toluene and isopropanol. Water was added as required to maintain the reaction volume.

The aqueous solution containing tris-phosphono ethyl phosphine was stripped on a rotary evaporator to give the product as a viscous oil.

Crystallisation from water/acetic acid gave the required product as a white crystalline substance.

Found: Equivalent weight (by iodine titration in Na$_2$HPO$_4$ aqueous buffer): 356
Calculated: (for P[CH$_2$CH$_2$PO$_3$H$_2$]$_3$): 358
Found:
C: 19.69%
H: 4.98%
P: 34.0%
Calculated:
C: 20.1%
H: 5.02%
P: 34.6%

The phosphine is stable in air and appears to exist as the Zwitterion

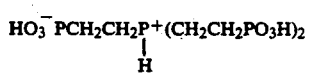

the Zwitterion was characterised by $^{31}$P nmr:

$P_I\delta = 19.23$ ppm; 1:3:3:1 quartet
$^3J_{P-P} = 54.8$ Hz
$P_{II}\delta = 22.7$ ppm; 1:1 doublet
$^3J_{P-P} = 54.8$ Hz
Relative integral of $P_I$:$P_{II}$ was 3:1
We claim:

1. A process for the preparation of organophosphines comprising reacting
   (i) a phosphine gas with
   (ii) an ethylenically-unsaturated compound selected from the group consisting of alicyclic hydrocarbons, aliphatic hydrocarbon alcohols and vinyl phosphonic acid esters,
   in the presence of a free-radical intiator and at ambient pressure, said process carried out by the following steps:
   (a) passing said phosphine gas into a solution of said compound (ii) in an amount effective to saturate said solution with said phosphine gas;
   (b) adding said free-radical initiator to said solution;
   (c) initiating the reaction of said phosphine gas with said compound (ii) and
   (d) continuing to pass further amounts of said phosphine gas into said solution to complete the reaction.

2. The process of claim 1, wherein said reactant (ii) is selected from the group consisting of oct-1-ene, hex-1-ene, but-1-ene, isobutene, allyl alcohol, esters of vinyl phosphonic acid, norbornene, norbornadiene, dicyclopentadiene, diisobut-1-ene and cyclooctadiene.

3. The process of claim 2, wherein said free-radical initiator is selected from the group consisting of peroxidic radical-forming agents and azo compounds.

4. The process of claim 3, wherein the reaction is initiated by ultraviolet radiation.

5. The process of claim 4, wherein the reaction is carried out at a temperature of from −50° C. to +60° C.

6. The process of claim 5, wherein said initiator is azo-bis-dimethylvaleronitrile and the radiation has a wavelength of 300 to 400 nm.

7. The process of claim 3, wherein the reaction is initiated by heating to a temperature of 60° to 140° C.

8. The process of claim 7, wherein the reaction is initiated by heating to a temperature of 60° C. to 90° C. and the initiator is azo-bis-dimethylvaleronitrile.

9. The process of claim 1, wherein said free-radical initiator is selected from the group consisting of peroxidic radical-forming agents and azo compounds.

10. The process of claim 9, wherein said initiator is azo-bis-dimethylvaleronitrile.

11. The process of claim 1, wherein the reaction is initiated by means of ultra violet radiation.

12. The process of claim 11, wherein the radiation has a wavelength of from 300 to 400 nM.

13. The process of claim 11, wherein the reaction is carried out at a temperature of from −50° C. to +60° C.

14. The process of claim 1, wherein the reaction is initiated by means of external heating.

15. The process of claim 14 wherein the heating is at a temperature in the range of 60°–140° C.

16. The process of claim 15, wherein the heating is at a temperature in the range of 60°–90° C.

* * * * *